(12) United States Patent
Gómez Álvarez et al.

(10) Patent No.: US 10,918,111 B2
(45) Date of Patent: Feb. 16, 2021

(54) ANTIMICROBIAL COMPOSITION FOR COATING SURFACES

(71) Applicant: ATACAMALAB SPA, Santiago (CL)

(72) Inventors: Marisol Gómez Álvarez, Santiago (CL); Claudio Guillermo Ramírez Mora, Santiago (CL)

(73) Assignee: ATACANALAB, Santiago (CL)

( * ) Notice: Subject to any disclaimer, the term of this patent is extended or adjusted under 35 U.S.C. 154(b) by 0 days.

(21) Appl. No.: 15/779,267

(22) PCT Filed: Dec. 29, 2016

(86) PCT No.: PCT/CL2016/050082
§ 371 (c)(1),
(2) Date: May 25, 2018

(87) PCT Pub. No.: WO2017/113033
PCT Pub. Date: Jul. 6, 2017

(65) Prior Publication Data
US 2019/0246644 A1 Aug. 15, 2019

(30) Foreign Application Priority Data

Dec. 29, 2015 (WO) ................ PCT/CL2015/050058

(51) Int. Cl.
| | | |
|---|---|---|
| *A01N 59/20* | (2006.01) | |
| *B05D 1/02* | (2006.01) | |
| *B22F 1/02* | (2006.01) | |
| *A61K 33/34* | (2006.01) | |
| *A61K 6/17* | (2020.01) | |
| *A01N 25/10* | (2006.01) | |
| *B05D 3/00* | (2006.01) | |
| *B05D 3/14* | (2006.01) | |
| *B05D 1/12* | (2006.01) | |

(52) U.S. Cl.
CPC .............. *A01N 59/20* (2013.01); *A01N 25/10* (2013.01); *A61K 6/17* (2020.01); *A61K 33/34* (2013.01); *B05D 1/02* (2013.01); *B05D 3/007* (2013.01); *B05D 3/14* (2013.01); *B22F 1/02* (2013.01); *B05D 1/12* (2013.01)

(58) Field of Classification Search
CPC .......... A61K 6/17; A61K 33/34; A01N 59/20; A01N 25/10; B05D 1/02; B05D 1/12; B05D 3/007; B05D 3/14; B22F 1/02
See application file for complete search history.

(56) References Cited

U.S. PATENT DOCUMENTS

| | | | | |
|---|---|---|---|---|
| 4,908,381 | A | * 3/1990 | Greenwald | ............ A01N 25/24 514/460 |
| 2006/0207385 | A1 | 9/2006 | Goia et al. | |
| 2006/0210807 | A1* | 9/2006 | Miller | .................... C08G 18/60 428/423.1 |
| 2015/0147584 | A1 | 5/2015 | Yamada et al. | |

FOREIGN PATENT DOCUMENTS

| | | | |
|---|---|---|---|
| CL | 201500921 A1 | 10/2015 | |
| EP | 1787742 A1 | 5/2007 | |
| EP | 2345329 A2 | 7/2011 | |
| JP | 61053206 | * 3/1986 | |
| WO | 2009102825 A1 | 8/2009 | |
| WO | 2014025949 A2 | 2/2014 | |

OTHER PUBLICATIONS

Mohamed Ali Ben Aissa et al., "Copper nanoparticles of well-controlled size and shape: a new advance in synthesis and self-organization." Nanoscale, The Journal of Royal Society of Chemistry, vol. 7, 2015, pp. 3189-3195.

Alvarez M.P. et al., "Estudio De Las Propiedades Eléctricas, Mecánicas Y Temperatura De Transición Vítrea De Compósitos Cobre-Polimetacrilato De Metilo.", Congreso Sam/Conamet, Sep. 4, 2007 (Sep. 4, 2007), pp. 1198-1204.

PCT International Search Report (w/Machine Translation), dated Apr. 13, 2017 (Apr. 13, 2017), for related PCT International Application No. PCT/CL2016/050082 (pp. 9).

Written Opinion of the International Searching Authority (w/Machine Translation), dated Apr. 13, 2017 (Apr. 13, 2017), or related PCT International Application No. PCT/CL2016/050082 (pp. 15).

* cited by examiner

*Primary Examiner* — Ali Soroush

(74) *Attorney, Agent, or Firm* — Defillo & Associates; Evelyn A. Defillo

(57) ABSTRACT

The present invention provides an antimicrobial composition for coating surfaces that enables a reduction of up to one hundred percent of the microbial activity on any type of frequently used substrate or surface, comprising a compound of micronized high-purity metallic copper particles. Moreover, a process for preparing the composition is provided.

8 Claims, 3 Drawing Sheets

ANTIMICROBIAL COMPOSITION FOR COATING SURFACES

TECHNICAL FIELD

The present invention provides an antimicrobial composition for coating surfaces that enables a reduction of up to one hundred percent of the microbial activity on any type of frequently used substrate or surface.

Moreover, a process for preparing the composition is provided.

BACKGROUND

It has been demonstrated by studies that healthcare-associated infections (HAIs) pose a public health problem given that they increase the morbidity and mortality of patients as well as the costs of care. It is estimated that 70,000 cases of hospital-acquired illnesses occur in Chile each year, which translates into substantial cost for the country. Various studies point out that some of these HAIs originate from the transmission of pathogens via contact surfaces such as floors, walls, the side rails of beds, tables, etc. This problem provides an opportunity to innovate in the area of materials that have antimicrobial properties and that can replace conventional objects and surfaces and thereby have a great impact both in terms of health and economics.

In 2008, the Environmental Protection Agency (EPA of the United States approved the registration of alloys of antimicrobial copper, confirming that they are beneficial to public health. These bactericidal properties of copper have already been put to use in hospitals in Europe, the United States, and Chile, and it has been demonstrated that copperized surfaces reduce the pathogen load. However, metallic copper materials have certain drawbacks, such as oxidation, high cost, and difficult processability, which limits their implementation. The above drawbacks can be overcome by developing plastic (polymeric) materials and coatings (paints, varnishes, gels) to which antimicrobial properties are imparted through the incorporation of copper-based compounds.

In this way, various researchers have demonstrated, in applying the criteria established by the EPA (Environmental Protection Agency), that surfaces made of copper or alloys thereof are capable of eliminating 99.9% of pathogenic bacteria within hours, including methicillin-resistant *Staphylococcus aureus* (MRSA), *Escherichia coli* O157:H7, *Pseudomonas aeruginosa*, *Enterobacter aerogenes*, *Listeria monocytogenes*, *Salmonella entérica*, *Campylobacter jejuni*, *Legionella pneumophila*, *Clostridium difficile*, and *Mycobacterium tuberculosis*.

Consistent findings under the conditions established by the EPA demonstrate the effectiveness of copper in the elimination of pathogenic bacteria at room temperature, in contrast to stainless steel. In these studies, copper quickly eliminated MRSA in 90 minutes, whereas no decrease in the bacterial concentration was observed with stainless steel after 6 hours (360 minutes). In the alloy bronze, which contains 80% copper, MRSA was completely eliminated in 270 minutes.

Laboratory evidence documents the efficacy of copper in eliminating spores and vegetative forms of *Clostridium difficile*, a hospital pathogen associated with outbreaks of hospital-acquired infections with high mortality. These studies have shown elimination of spores after 24 hours of exposure to metallic copper, and another study shows that this effect occurs beginning after 30 minutes for vegetative forms and at 3 hours for spores, even in the presence of organic matter.

It is important to highlight that the bactericidal effect of copper surfaces is directly proportional to the concentration, with the maximum effect being achieved with metallic copper (99.9%) and being maintained in alloys containing at least 70% copper, and that, in these concentrations, it is also capable of inhibiting the formation of biofilms or multicellular colonies that are surrounded by extracellular polymers that they use in order to facilitate adhesion and the colonization of surfaces.

And so it was that, on 25 Mar. 2008, with the support of the cumulative scientific evidence, the EPA registered copper as the first and only metal with antibacterial properties, authorizing the dissemination of significant concepts, including the fact that "copper surfaces eliminate 99.9% of bacterial pathogens after 2 hours of exposure" and certifying the fact that surfaces made of metallic copper and alloys thereof are natural antimicrobial agents, have long-lasting antimicrobial efficacy, have a self-disinfecting effect, and are superior to other coatings that are available on the market.

This registration authorizes the use of copper surfaces in hospital environments.

In addition, laboratory studies conducted by the Universidad de Chile have shown that copper surfaces not only kill bacteria by direct contact, but also impede the adhesion and inhibit the reproduction of clinical strains of the primary agents associated with hospital-acquired infections, including MRSA, multiresistant *Klebsiella pneumoniae*, and multiresistant *Acinetobacter baumanii*, in contrast to what is observed on stainless steel surfaces, to which bacteria adhere rapidly and very efficiently.

The precise mechanism explaining the antibacterial activity of copper has not been completely elucidated. One crucial element of the antibacterial activity is the ability of copper to give off and accept electrons in a continuous process. Some studies suggest that, in high concentrations, copper has a toxic effect on bacteria due to the release of hydroperoxide radicals; the copper ions may potentially substitute ions that are essential to bacterial metabolism, such as iron, initially interfering with the function of the cell membrane and then, in the cytoplasm, altering the protein synthesis, whether by inhibiting the formation of proteins or causing the synthesis of dysfunctional proteins, thus altering the activity of enzymes that are essential to bacterial metabolism[12, 13].

Copper has also exhibited the ability to destroy viruses that are of great medical importance, including the influenza A virus and the human immunodeficiency virus, HIV, in concentrations as low as 0.16 to 1.6 mM. The development of filters with copper oxide has made it possible to efficiently eliminate the risk of the transmission of HIV via fluids[14]. The mechanisms involved in the antiviral activity are the inactivation of a protease enzyme that is important to viral replication and the damaging of the phospholipid shell[14-16].

On the other hand, evidence also exists of the antifungal activity of copper. For example, species of fungi, including *Candida albicans*, are inhibited in their growth and then destroyed when they come into contact with copper surfaces. The antifungal activity probably occurs by means of a complex process called "death by contact," in which the cytoplasmic membrane is damaged and becomes depolarized, facilitating the entry of copper ions into the cell, augmenting the damage and, secondarily, producing an increase in the oxidative stress without apparent damage.

In the prior art, it is possible to find coatings and compositions describing the use of copper, such as document GB 2466805, which describes a method for the deposition of a layer with antibacterial properties onto a substrate that comprises chemical vapor deposition at atmospheric pressure using a flame as a reaction energy source; a second metal for stabilizing, protecting, and controlling the release of the metal is also deposited, with the metal and the second metal being deposited simultaneously or successively.

It is also possible to find compositions with antimicrobial agents against gram-positive and gram-negative microorganisms that correspond to nanoparticles of copper and nanoparticles of copper oxide, as described in the publication RU 2416435, in which the antimicrobial agents according to the invention are characterized by specific particle sizes and phase compositions. The nanoparticles contain 67 to 96% of copper and 4 to 33% of CuO. The nanoparticles of copper oxide contain crystalline copper, CuO and $Cu_2O$.

As regards the use of nanoparticles and polymers, the publication WO 2014030123 relates to polymeric materials, particularly thermoplastic or resins with antifouling, biocidal, antiviral, and antimicrobial properties, wherein the antimicrobial property is given by the controlled and maintained release over time of elements or compounds with antimicrobial properties comprising nanoparticles from 4 to 500 nanometers, more preferably from 10 to 80 nanometers, of an element or inorganic compound with antimicrobial and biocidal properties, wherein the nanoparticles are pre-treated to improve final dispersion and are completely embedded in the thermoplastic resin and do not protrude from the surface of the resin, and wherein the nanoparticles of the element or inorganic compound with antimicrobial properties form a secondary structure, called an agglomerate, ranging in size from 0.1 to 100 micrometers, wherein the ratio in weight between nanoparticles of the element or inorganic compound and the thermoplastic and/or thermostable resin and/or organic coating of painting type is between 1 and 80% by weight, and wherein said secondary structures are homogeneously dispersed in the resin.

Products are thus known that are based on the antimicrobial activity of copper for use in marine transport but that are highly toxic to humans.

By significantly reducing the bacterial load, copper enables aseptic conditions in clinical enclosures and in schools, and in public spaces in general, to be enhanced, helping to reduce cross-contamination in food-related processes. Notwithstanding the above, what is certain is that no composition is known that is capable of reducing the microbial load by one hundred percent with copper particles in one hour.

The current limitations on the use of copper on surfaces lie in the high cost of using plates of metallic copper that do not have the appropriate dimensions for every surface, which results in high installation costs as well. In the case of the polymeric resins or coatings, the natural wear from use gradually eliminates the copper content of the surfaces, reducing their antimicrobial capacity.

Definitions

Micrometric metallic copper particles: Refers to particles whose size is no less than 1 micrometer and no more than 1000 micrometers. This is to differentiate them from nanoparticles that are smaller than 1 micron and pieces of metal that are larger than 1000 microns.

100% solid resin: Refers to binding compounds that are free of volatile organic solvents.

BRIEF DESCRIPTION OF THE INVENTION

The present invention relates to an antimicrobial composition for coating surfaces and to a process for preparing said composition intended to address the problem of the possible shortcomings in the response time, efficiency, and efficacy of the asepsis of surfaces that may have microbial activity.

The composition and process are based on the combination of copper particles and solvent-free binding agents that enable the coating to adhere to the substrate to which it is applied with the purpose of obtaining a covered surface that is capable of eliminating the microbial activity on the surfaces exposed to the composition by up to one hundred percent.

The composition operates in three phases or stages that interact so as to facilitate the antimicrobial action of the copper particles, enabling the surfaces to which it is applied to be used without the risk of contamination or contagion by microbes.

DETAILED DESCRIPTION OF THE INVENTION

The invention corresponds to an antimicrobial composition for coating surfaces, being a micronized and micrometric high-purity metallic copper compound, with a distribution of particles of various shapes, sizes, and proportions in a fluid vehicle to be applied cold and hardened by polymerization mechanisms.

The particles that are used have 4 main shapes:
spherical,
filamentous,
amorphous, and
laminar.

Figure 1:
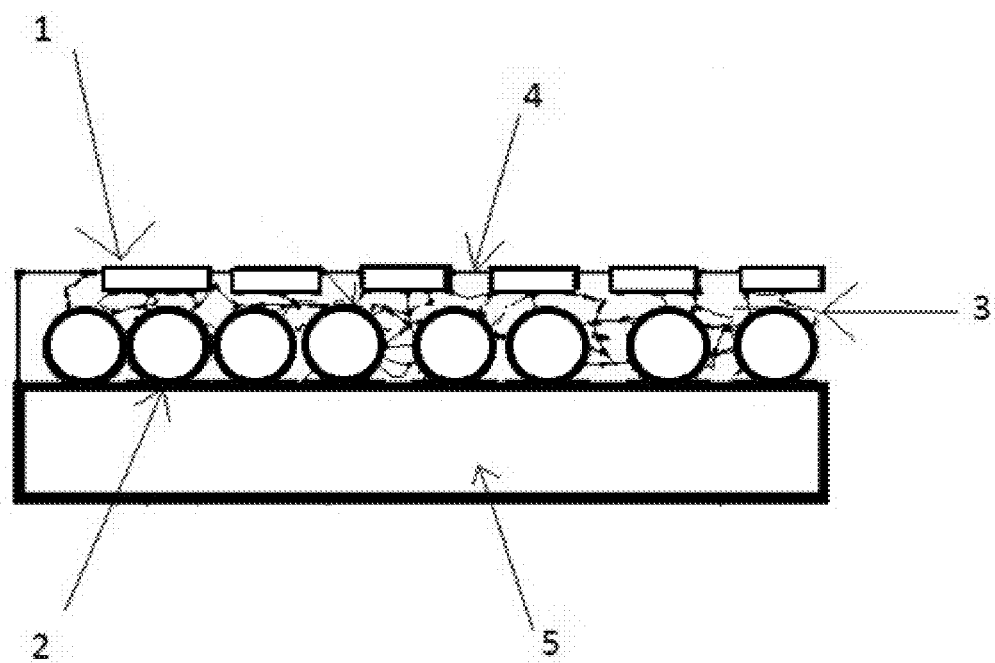
FIG. 1: Schematic diagram of the distribution of the particles in the composition once applied to the surface: 1.—Laminar particles. 2.—Spherical particles. 3.—Filamentous and nanometric particles. 4.—Polymerization vehicle. 5.—Substrate to which it is applied.

The size distribution ranges from 1 micrometer to 50 microns. The diversity of the shapes and sizes of the metallic particles enables surfaces to be obtained having up to 100% antimicrobial protection, as shown in FIG. 1.

Unlike other coating-type products that contain particles, nanoparticles, or pigmentations of copper and other active substances that act as biocides or bactericides, the inventive saturation of shapes and dimensions ensures permanent antimicrobial action over time on the basis of high-density metallic copper, which renders it distinctive and differentiating, since it is equivalent or superior in its functionality to the application of a metallic copper coating.

The antimicrobial action of the composition according to the present invention operates in three phases or stages that interact with one another:

The first phase corresponds to the mass of copper that carries the greatest ionic charge. This phase tends to be located in the lower zone that is in contact with the surface to be coated, since the largest or most massive particles travel to the bottom of the coating or to the interior of the coating.

The second phase corresponds to the surface of the coating where the laminar particles are located and that float in contact with the surface and the internal medium of the coating. These particles have a low charge but greater surface exposure toward the exterior of the coating.

The third phase comprises the amorphous and/or filamentous copper particles that form the network for ion contact and transmission with the aid of the polymer, which acts as a binding vehicle for the copper particles. These particles have little mass and little surface area, but they act as a bridge of communication between the surface laminar particles and the particles with a high charge contribution.

This combination of 4 different types of copper particle and the polymer thus facilitate the antimicrobial action of the copper by facilitating the ionic capacity of the material, thus enabling antimicrobial action to be achieved that is up to 100% effective, making it possible for the surfaces to which it is applied to be used without the risk of contamination or contagion by microbes. This improved ionic effect is therefore due to the geometry of the particles and the distribution thereof in combination with the polymer.

As regards the copper content of the composition, it is greater or equal to 30% and up to 90% with respect to the weight of the final composition.

The polymer corresponds to a binder that is free of solvent, 100% solid, hardened by crosslinking, and capable of adhering well to the surface to be coated or substrate. The use of a polymer enables a coating to be obtained that covers the entire shape or geometry of the substrate with ease.

The polymers to be used include epoxy coatings such as polyamide epoxy resin, polyurethane, and polymethyl methacrylate, among others.

Process for Preparation:

The particles are prepared by means of thermal induction melting processes and subsequent pulverization in inert gas media at low temperature in order to prevent metal oxidation. Spherical and hemispherical particles are obtained in this way which are screened in order to obtain particles in the granulometric range between 1 micron and 50 microns, with a mean of 25 microns.

A fraction of these particles, preferably between 10 and 20% of such particles, is separated and treated in ball and roller mills in order to obtain the laminar and amorphous particles. The filamentous particles have a weight of up to 10% of the total weight of the particles and are obtained independently from the other types of particle by means of techniques using microwires obtained by melting copper inside glass capillaries, which are wound on a spool from which they are cut in lengths of less than 50 microns.

To produce the coating, premixing is performed only of the laminar particles, which provide the characteristic copper color, stabilized with the additive zinc phosphate, and with the resin, which contains thixotropic additive of the pyrogenic siliceous type. The larger-sized spherical and hemispherical particles are incorporated subsequently and alone at the moment the product is prepared and within the "mixing lifetime" of the resin with the hardener, for which reason they are delivered in an accompanying container. This finally results in a product with 3 components—the pigmented base, hardener, and system-activating particles.

Manner of Application and Mechanism of Action

To apply the composition, the first step is to make a preparation and clean the substrate to which the composition is to be applied. The resin base, which contains the thixotropic and stabilizing additives of Zn phosphate with the larger-sized activator particles, is then mixed, and then it is mixed with the hardening reagent. The composition is applied using airless equipment (airless projection).

The product that is applied does not contain solvents and contains copper particles that float in contact with the surface and the internal medium of the coating.

Once the surface to which the coating was applied has been cleared for use, an electrostatic activation process is performed after which it begins to release its antimicrobial capacity.

The precise mechanism explaining the antibacterial activity of copper has not been completely elucidated. However, one crucial element of the antibacterial activity is the ability of copper to give off and accept electrons in a continuous process.

Some studies suggest that, in high concentrations, copper has a toxic effect on bacteria due to the release of hydroperoxide radicals; the copper ions may potentially substitute ions that are essential to bacterial metabolism, such as iron, initially interfering with the function of the cell membrane and then, in the cytoplasm, altering the protein synthesis, whether by inhibiting the formation of proteins or causing the synthesis of dysfunctional proteins, thus altering the activity of enzymes that are essential to bacterial metabolism.

The sequence in which the copper particles act on the bacteria is:

1. Copper ions are released from copper surfaces, penetrating the bacterial cell and causing damage to the cytoplasmic membrane.
2. Rupturing of the cytoplasmic membrane promotes the entry of the copper ions, which results in dysfunction of the membrane and an increase in the oxidative stress.
3. An alteration of the protein synthesis is produced in the cytoplasm, along with functional damaging of the essential enzymes.
4. Cell death and degradation of bacterial DNA.

Technical Advantages

Since this is micrometric and not nanometric copper, it is not toxic to users who are exposed to the coated surfaces.

The resulting coating attains high levels of wear resistance and complete adhesion to a variety of substrates, offering 100% antibacterial protection against the bacteria defined in the standard or protocol of the Environmental Protection Agency (EPA).

The composition according to the present invention is free of solvents, which renders it safe in comparison to alternative products, which contain active ingredients that are possibly toxic and solvents that limit the application thereof in closed spaces and are not safe for use on surfaces that are in direct contact with users.

Another advantage lies in the fact that application can be performed at low temperature, making it suitable for all surface types and reducing the application costs in comparison to products with a similar copper content, which are applied at high temperatures.

PREFERRED EMBODIMENT OF THE INVENTION

Although the resin contains thixotropic additives, it was found that, due to the density and shape of the larger-sized spherical and filamentous particles, they sediment out a few days after having been incorporated; for this reason, the resin base is delivered with thixotropic additives of pyrogenic silica and Zn phosphate additives that stabilize the oxidation of Cu together with the laminar particles in a proportion of 1 to 3%. The spherical particles on the order of 50 microns are delivered separately in order to be incorporated only at the time of application simultaneously with the hardener; between 30 and 90% by weight of spherical particles of high-purity metallic copper are incorporated. The lifetime of the mix is less than one hour at 20° C., with the lifetime decreasing at higher temperatures.

EXAMPLES

Example 1: Quantification of the Antibacterial Activity of Specimens with "Liquid Copper" Coating (Laboratory Report)

The following data are from the analyses performed on 25 Sep. 2015 by David Montero, M. Sc., Ph.D. (c) at the inventors' request.
Methodology: Protocol for the Analysis of Antibacterial Activity on Solid Surfaces that Contain Copper.

The protocols described by the United States Environmental Protection Agency (EPA) were used in order to determine the disinfectant efficacy of surfaces containing copper,[1] with slight modifications.

The target samples (type A: A1, A2, A3; type B: B1, B2, B3) were briefly sterilized with sodium hypochlorite (20% v/v) and ethanol (70% v/v) for 24 hours. Each specimen was then placed in a plastic petri dish and allowed to dry in a laminar flow chamber for 1 hour, with UV radiation being applied to each side for 15 minutes.

Each specimen was evaluated using an inoculum of *Escherichia coli* O157:H7 (ATCC 43895) or *Staphylococcus aureus* (ATCC 29213) containing between $1 \times 10^7$ and $5 \times 10^7$ bacteria.

The inocula of *E. coli* and *S. aureus* were obtained by growing the bacteria overnight on Luria Bertani (LB) agar and brain heart infusion agar, respectively. One hour post-inoculation, each specimen was washed with 1 ml of saline phosphate buffer solution (PBS), and the bacterial count was performed by means of dilution series.

The bacterial count for *E. coli* and *S. aureus* was performed by plating 10 μl of each dilution on LB agar and Baird Parker agar, respectively.

The LB agar and Baird Parker agar plates were incubated at 35±2° C. for 24 and 48 hours, respectively. The plates containing between 10 and 200 colony-forming units (CFUs) were recorded. The evaluation was performed in experimental and technical duplicate.
Data Analysis:
Number of viable bacteria per specimen:

$$N=(C \times D \times V)/V_2$$

where
N=number of viable bacteria recovered per test specimen
C=average count for specimens in duplicate
D=dilution factor for each plate counted
V=volume of PBS added for each specimen, in ml
$V_2$=plated volume, in ml
Percentage Reduction:

$$\% \text{ reduction}=[(a-b)/a] \times 100$$

where
a=average initial inoculum or number of viable bacteria recovered in the control specimens
b=average number of viable bacteria recovered in the target specimens
Results
1. Antibacterial Activity Against *E. coli* O157:H7
Inoculum Used:
Assay 1.

$$N=(C \times D \times V)/V_2$$

$$N=((25+14)(10000)(1 \text{ ml}))/0.01 \text{ ml}$$

$$N=1.95 \times 10^7$$

Assay 2.

$$N=((22+26)(10000)(1 \text{ ml}))/0.01 \text{ ml}$$

$$N=2.4 \times 10^7$$

Figure 2:
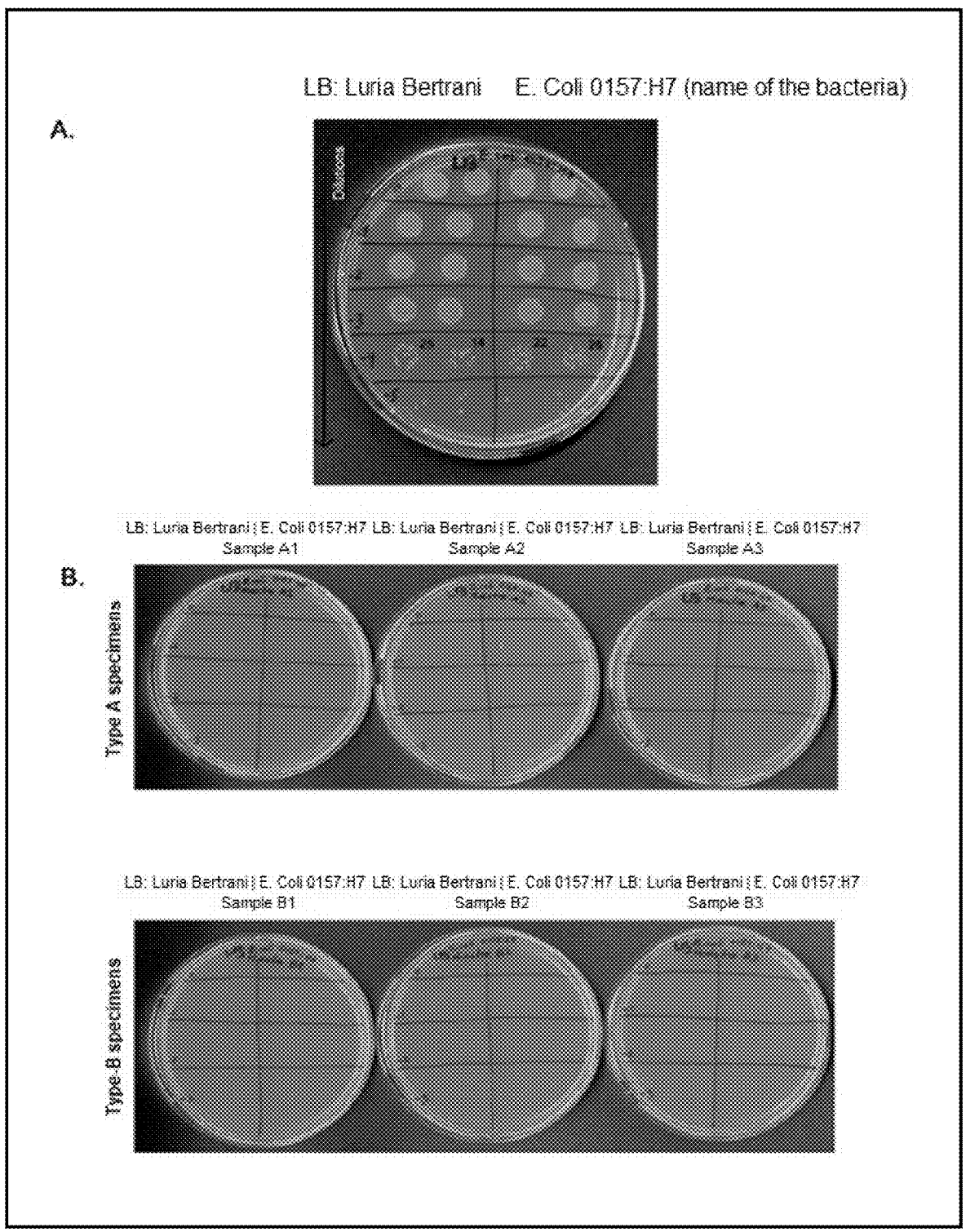
FIG. 2: Initial inoculum and CFU count for assay of antibacterial activity against *E. coli* O157:H7. [A] Initial inocula of $1.95 \times 10^7$ bacteria (assay no. 1, left) and of $2.4 \times 10^7$ bacteria (assay no. 2, right) [B] Viable bacterial count for each specimen. Experimental and technical duplicates are shown. The dilation factor is shown as 0, −1, −2, −3, −4, and −5.

For the first assay, an inoculum of $1.95 \times 10^7$ bacteria (FIG. 2A, left), and an inoculum of $2.4 \times 10^7$ bacteria was used for the second assay (FIG. 2A, right)
Viable Bacterial Count Per Specimen:
In all of the assays performed with type-$A_{1-3}$ and type-$B_{1-3}$ samples, no viable bacteria were observed after one hour of contact (FIG. 2B). Consequently, the reduction in the bacterial load was 100%.
2. Antibacterial Activity Against *S. aureus*
Inoculum Used:
Assay 1.

$$N=((43+44)(10000)(1 \text{ ml}))/0.01 \text{ ml}$$

$$N=4.35 \times 10^7$$

Assay 2.

$$N=((12+18)(10000)(1 \text{ ml}))/0.01 \text{ ml}$$

$$N=1.5 \times 10^7$$

Figure 3:
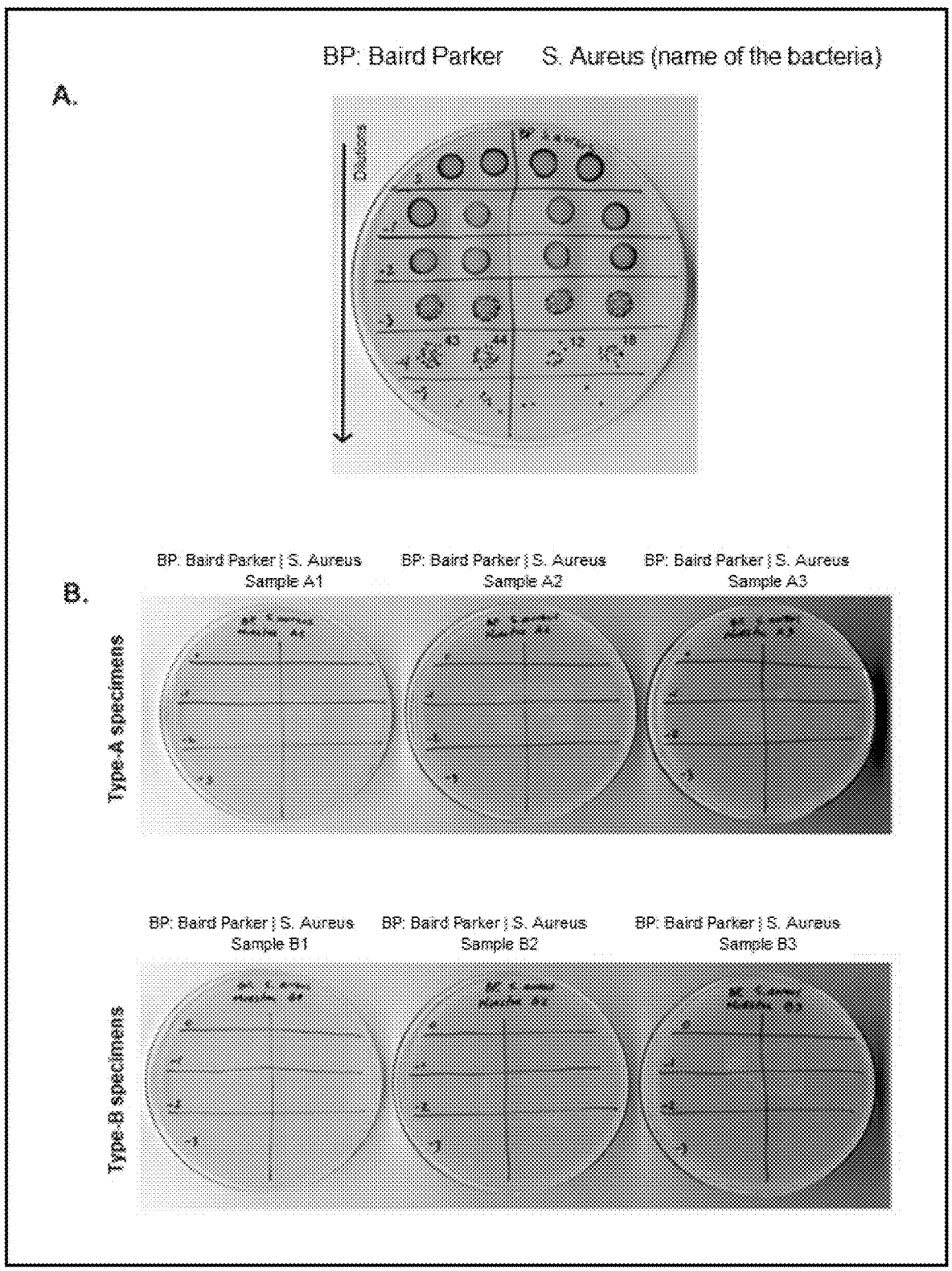
FIG. 3: Initial inoculum and CFU count for assay of antibacterial activity against *S. aureus*. [A] Initial inocula of $4.35 \times 10^7$ bacteria (assay no. 1, left) and of $1.5 \times 10^7$ bacteria (assay no. 2, right) [B] Viable bacterial count for each specimen. Experimental and technical duplicates are shown. The dilation factor is shown as 0, −1, −2, −3, −4, and −5.

For the first assay, an inoculum of $4.35 \times 10^7$ bacteria (FIG. 3A, left), and an inoculum of $1.5 \times 10^7$ bacteria was used for the second assay (FIG. 3A, right)
Viable Bacterial Count Per Specimen:
In all of the assays performed with type-$A_{1-3}$ and type-$B_{1-3}$ samples, no viable bacteria were observed after one hour of contact (FIG. 2B). Consequently, the reduction in the bacterial load was 100%.

The findings suggest that the type-A and type-B specimens can be preliminarily categorized as having disinfectant effect against *E. coli* O157:H7 and *S. aureus* when the described methodological protocol is implemented. More studies and replications are needed to corroborate the results obtained.

REFERENCES

[1] United States Environmental Protection Agency (EPA). 2014. Protocol for the Evaluation of Bactericidal Activity of Hard, Non-porous Copper/Copper-Alloy Surfaces. EPA, Washington, D.C.

The invention claimed is:

1. An antimicrobial composition for coating surfaces comprising:
   a compound of micronized high-purity metallic copper particles, wherein the compound of micronized metallic copper particles comprises a distribution of particles of different shapes, sizes, and proportions; and
   a fluid compound vehicle to be applied cold;
   where the micronized metallic copper particles comprise;
   spherical, hemispherical, and amorphous particles located in a lower zone of the coating that is in contact with the surface to be coated;
   laminar particles located in a top zone of the coating that is in contact with an external medium; and
   filamentous and amorphous particles located in an intermediate zone of the coating.

2. The composition as set forth in claim 1, wherein the fluid vehicle compound is a polymer that is hardened by mechanisms of polymerization.

3. The composition as set forth in claim 1, wherein the size distribution of the copper particles ranges from 1 nanometer to 50 microns.

4. The composition as set forth in claim 1, wherein the copper content in the composition is between 30% and 90% with respect to the weight of the final composition.

5. The composition as set forth in claim 2, wherein the polymer is free of solvent after the hardening.

6. The composition as set forth in claim 2, wherein the polymer is an inorganic resin selected from the group consisting of a polyamide epoxy, a polyurethane, and a polymethyl methacrylate.

7. The composition as set forth in claim 1, further including zinc phosphate as an additive.

8. The composition as set forth in claim 1, wherein the fluid vehicle contains a thixotropic resin of the pyrogenic siliceous type.

* * * * *